US010595881B2

(12) United States Patent
Wolford et al.

(10) Patent No.: US 10,595,881 B2
(45) Date of Patent: Mar. 24, 2020

(54) ORTHOPAEDIC REAMER SYSTEM

(71) Applicant: Symmetry Medical Manufacturing, Inc., Warsaw, IN (US)

(72) Inventors: Todd A. Wolford, Goshen, IN (US); Mark A. Nordman, Burket, IN (US); Arif H. Bin Jalalluddin, Fort Wayne, IN (US); David J. Whitehead, Goshen, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 212 days.

(21) Appl. No.: 15/728,652

(22) Filed: Oct. 10, 2017

(65) Prior Publication Data

US 2019/0105061 A1 Apr. 11, 2019

(51) Int. Cl.
*A61B 17/16* (2006.01)
*A61B 17/00* (2006.01)
*A61B 17/17* (2006.01)

(52) U.S. Cl.
CPC ...... *A61B 17/1624* (2013.01); *A61B 17/1631* (2013.01); *A61B 17/1633* (2013.01); *A61B 17/1666* (2013.01); *A61B 17/162* (2013.01); *A61B 17/1746* (2013.01); *A61B 2017/00477* (2013.01)

(58) Field of Classification Search
CPC .......... A61B 17/1624; A61B 17/1631; A61B 17/1633; A61B 17/1666; A61B 17/1664; A61B 17/162; A61B 17/1746; A61B 2017/00477; A61B 2017/320032
USPC .... 606/80, 87, 89, 79, 104, 180, 85, 99, 62, 606/88, 91, 53, 81
See application file for complete search history.

(56) References Cited

U.S. PATENT DOCUMENTS

| 6,875,217 B2 | 4/2005 | Wolford |
| 7,217,271 B2 * | 5/2007 | Wolford ............. A61B 17/1617 606/80 |
| 7,278,996 B2 | 10/2007 | Wolford |

(Continued)

FOREIGN PATENT DOCUMENTS

CH  710 378 A2  5/2016
WO  WO-2012136972 A1 * 10/2012 ........... A61B 17/162

OTHER PUBLICATIONS

Extended European Search Report dated Apr. 25, 2019 for European Patent Application No. 18 19 9172 (6 pages).

*Primary Examiner* — David W Bates
*Assistant Examiner* — Marcela I Shirsat
(74) *Attorney, Agent, or Firm* — Taylor IP, P.C.

(57) ABSTRACT

A driver for an orthopaedic reamer includes a drive shaft defining an axis of rotation; a reamer connector connected to the drive shaft and having at least one first annular portion about the axis of rotation and at least one second annular portion about the axis of rotation radially spaced from the at least first annular portion to define at least one holding recess therebetween; and a collar associated with the reamer connector and slidable in a direction of the axis of rotation between a first position and a second position, the collar being unaligned with the at least one holding recess circumferentially about the axis of rotation in the first position and, in the second position, being rotatably locked to the reamer connector and having a portion aligned with the at least one holding recess circumferentially about the axis of rotation.

16 Claims, 11 Drawing Sheets

(56) References Cited

U.S. PATENT DOCUMENTS

| | | | |
|---|---|---|---|
| 7,850,693 B2 | 12/2010 | Wolford | |
| 2007/0142840 A1* | 6/2007 | Goodwin | A61B 17/1666 606/81 |
| 2012/0023733 A1* | 2/2012 | Cannell | A61B 17/1617 29/525.01 |
| 2016/0089158 A1 | 3/2016 | Fortin et al. | |

* cited by examiner

ORTHOPAEDIC REAMER SYSTEM

BACKGROUND OF THE INVENTION

1. Field of the Invention

The present invention relates to orthopaedic instruments, and, more particularly, to orthopaedic reamers and associated drivers.

2. Description of the Related Art

In the field of orthopaedic surgery, it is often necessary to remove bone material and other tissue to enable implantation of a prosthesis to repair a joint in the human body. One particular instrument used to remove tissue from a joint is known in the art as a "reamer," which generally includes a semi-spherical shell with an arrangement of cutting openings on the surface of the shell and is connected to a driver which connects the reamer to a source of rotary motion to rotate the reamer and remove tissue.

A variety of constructions are known for connecting the reamer to the driver. One style of driver that is commonly used is known as the "Othy style" manufactured by Tecomet, Inc. which includes a crossbridge (also known as a bridgeback) element having a bar extending between the circumference of the hemisphere and having a circular expanded section in the middle. Another style of driver that is commonly used is known as a "cruciform reamer" manufactured by Greatbatch Medical and which has a crossbar shape in which two circular cross section bars intersect at the center and extend to the walls of the hemisphere.

While both the Othy style and cruciform reamer connectors are suitable for connecting a reamer to a source of rotary motion, recent developments in orthopaedic surgery have produced what are known as "hybrid" reamers. Examples of hybrid reamers are described in U.S. Pat. Nos. 7,850,693, 7,278,996, and 6,875,217 to Wolford, which replace the traditional crossbridge and cruciform constructions on the back of the reamer with attachment features that connect to a reamer connector. The attachment feature construction of the hybrid reamer taught by Wolford provides a secure connection between a reamer and a driver while reducing the incision size needed for the procedure, compared to a crossbridge or cruciform reamer, allowing the hybrid reamer to be suitable for both minimally invasive and open total hip arthroplasty. Further, eliminating the connection bars on the back of the reamer allows for increased visibility into the surgical site. While the hybrid reamer taught by Wolford is effective, a need remains for further improvements on the hybrid reamer design.

What is needed in the art is a hybrid reamer design which improves upon known hybrid reamer designs.

SUMMARY OF THE INVENTION

The present invention provides a reamer system including a collar associated with a reamer connector which can slide between a first position in which an orthopaedic shell can be rotated out of a holding recess of the reamer connector and a second position in which an orthopaedic shell can be rotatably locked within the holding recess.

The invention in one form is directed to a driver for an orthopaedic reamer including: a drive shaft defining an axis of rotation; a reamer connector connected to the drive shaft and having at least one first annular portion about the axis of rotation and at least one second annular portion about the axis of rotation radially spaced from the at least first annular portion to define at least one holding recess therebetween; and a collar associated with the reamer connector and slidable in a direction of the axis of rotation between a first position and a second position, the collar being unaligned with the at least one holding recess circumferentially about the axis of rotation in the first position and, in the second position, being rotatably locked to the reamer connector and having a portion aligned with the at least one holding recess circumferentially about the axis of rotation.

The invention in another form is directed to an orthopaedic reamer system including: a drive shaft defining an axis of rotation; a reamer connector connected to the drive shaft and having at least one first annular portion about the axis of rotation and at least one second annular portion about the axis of rotation radially spaced from the at least first annular portion to define at least one holding recess therebetween; an orthopaedic shell having an outer surface with a plurality of openings formed therein and at least one holding tab placed within the at least one holding recess; and a collar associated with the reamer connector and slidable in a direction of the axis of rotation between a first position and a second position, the at least one holding tab being rotatable out of the at least one holding recess when the collar is in the first position, the collar being rotatably locked to the reamer connector and rotatably locking the at least one holding tab within the at least one holding recess in the second position.

An advantage of the present invention is the holding recess can be shaped to hold a large portion of the holding tab to stably connect the orthopaedic shell to the reamer connector.

Another advantage is the collar can be a separable item from the reamer connector and drive shaft to allow for easy cleaning and sterilization.

Yet another advantage is the collar can be quickly switched between the first position and second position to allow for quick connection and disconnection of the orthopaedic shell from the reamer connector.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
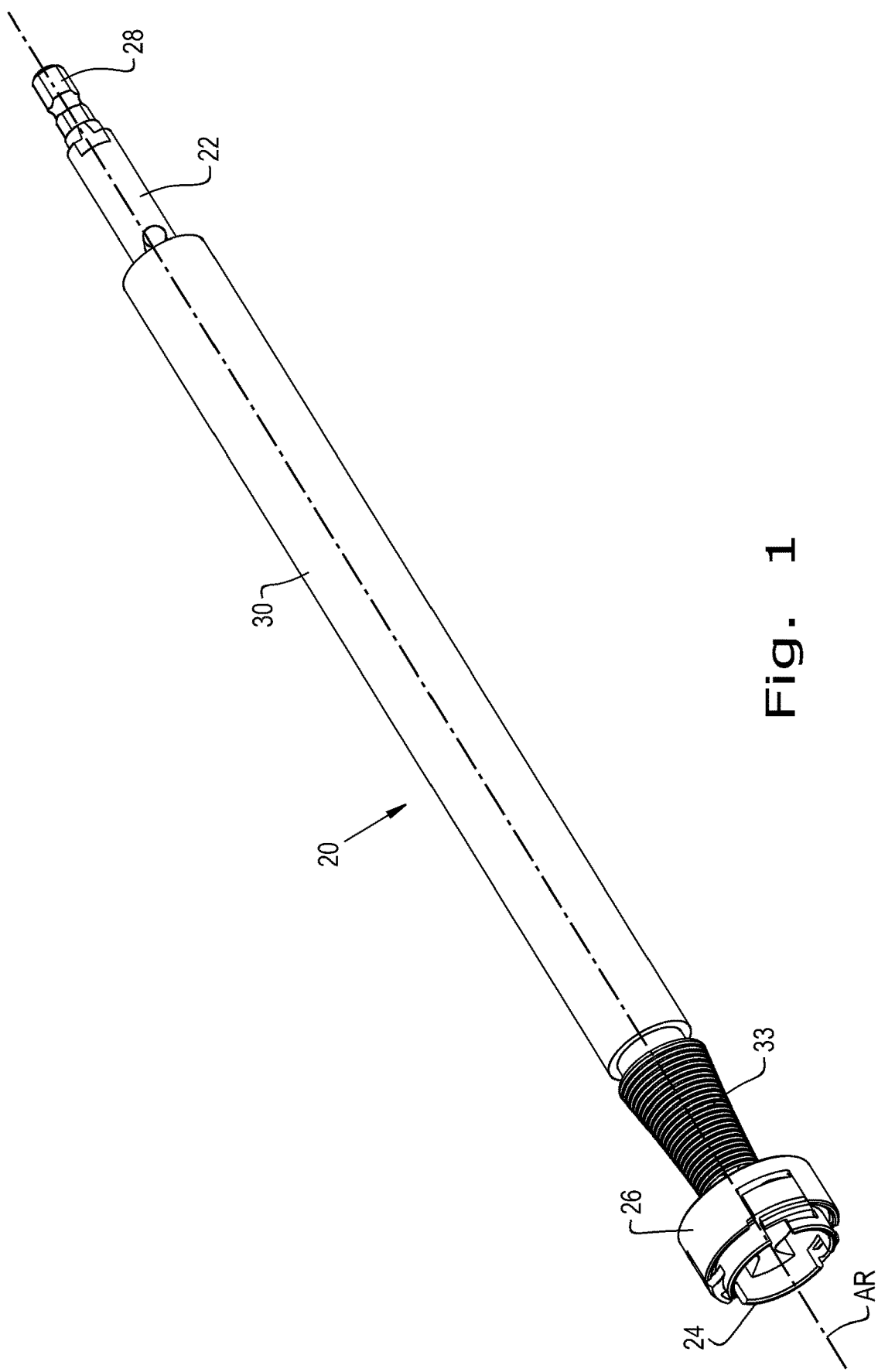
FIG. 1 is a perspective view of an exemplary embodiment of a reamer driver formed in accordance with the present invention.
Figure 2:
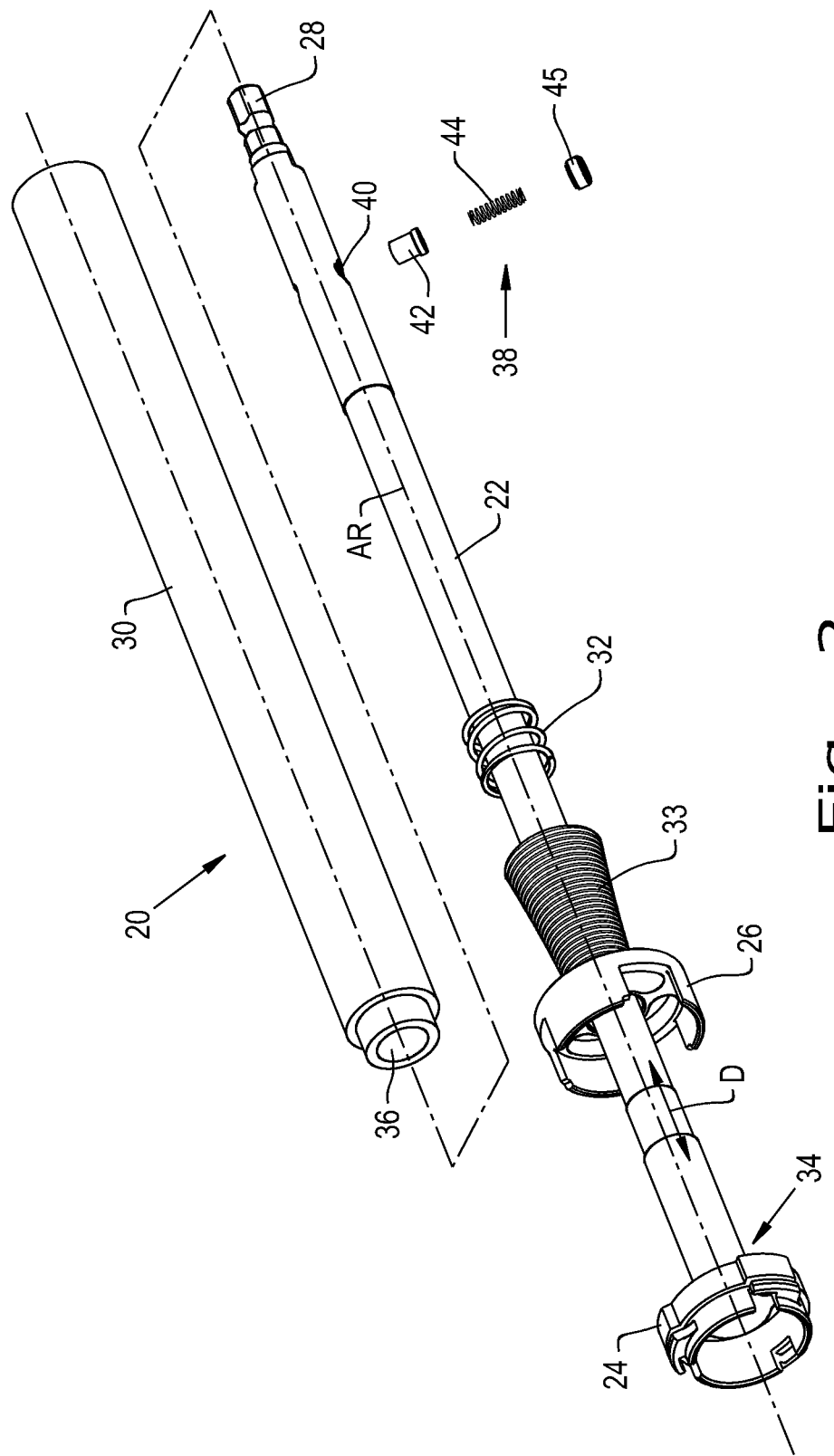
FIG. 2 is a partially exploded view of the reamer driver shown in FIG. 1.

Referring now to the drawings, and more particularly to FIGS. 1 and 2, there is shown an exemplary embodiment of a reamer driver 20 formed in accordance with the present invention which generally includes a drive shaft 22, a reamer connector 24 connected to the drive shaft 22, and a collar 26 associated with the reamer connector 24. As used herein, the collar 26 is "associated with" the reamer connector 24 in the sense that the collar 26 is located adjacent to the reamer connector 24 to interact with the reamer connector 24 in various positions of the collar 26, as will be described further herein. The drive shaft 22 can include a chuck 28 which is sized and shaped to interact with a rotary driver (not shown), such as a power drill, to rotate the drive shaft 22 about an axis of rotation AR defined by the drive shaft 22. The reamer driver 20 can also include a sleeve 30 placed and fitted over the drive shaft 22 and a biasing element 32, shown as a spring, which bears on the collar 26 and spring 32, the significance of which will be described further herein. A tapered pull back collar 33 which can include grooves (as shown) or knurling is positioned around the drive shaft 22, adjacent to the collar 26, and can either be integral with or separate from the drive shaft 22.

Referring now to FIG. 2, an exploded view of the reamer driver 20 is shown. As can be seen, the reamer connector 24 can be integrally formed with the drive shaft 22 at a reamer end 34 of the drive shaft 22 opposite the chuck 28 or, alternatively, can be separable from the drive shaft 22. The collar 26, on the other hand, is slidable in a direction along the axis of rotation AR, signified by the arrow D, such as axially along the drive shaft 22, toward and away from the reamer connector 24. As can be seen, the spring 32 can be integrally formed with the collar 26, but the spring 32 can also be a separate element if desired. The sleeve 30 can have a sleeve opening 36 formed therein which houses part of the drive shaft 22 while the sleeve 30 is placed over the drive shaft 22. The sleeve 30 can be secured to the drive shaft 22 by, for example, a spring-loaded pin assembly 38 fitted inside a pin opening 40 formed in the drive shaft 22 and including a pin 42 biased out of the pin opening 40 by a pin spring 44 and set screw 45, with a user depressing the pin 42 into the pin opening 40 to allow the sleeve 30 to slide off the drive shaft 22.

Figure 3:
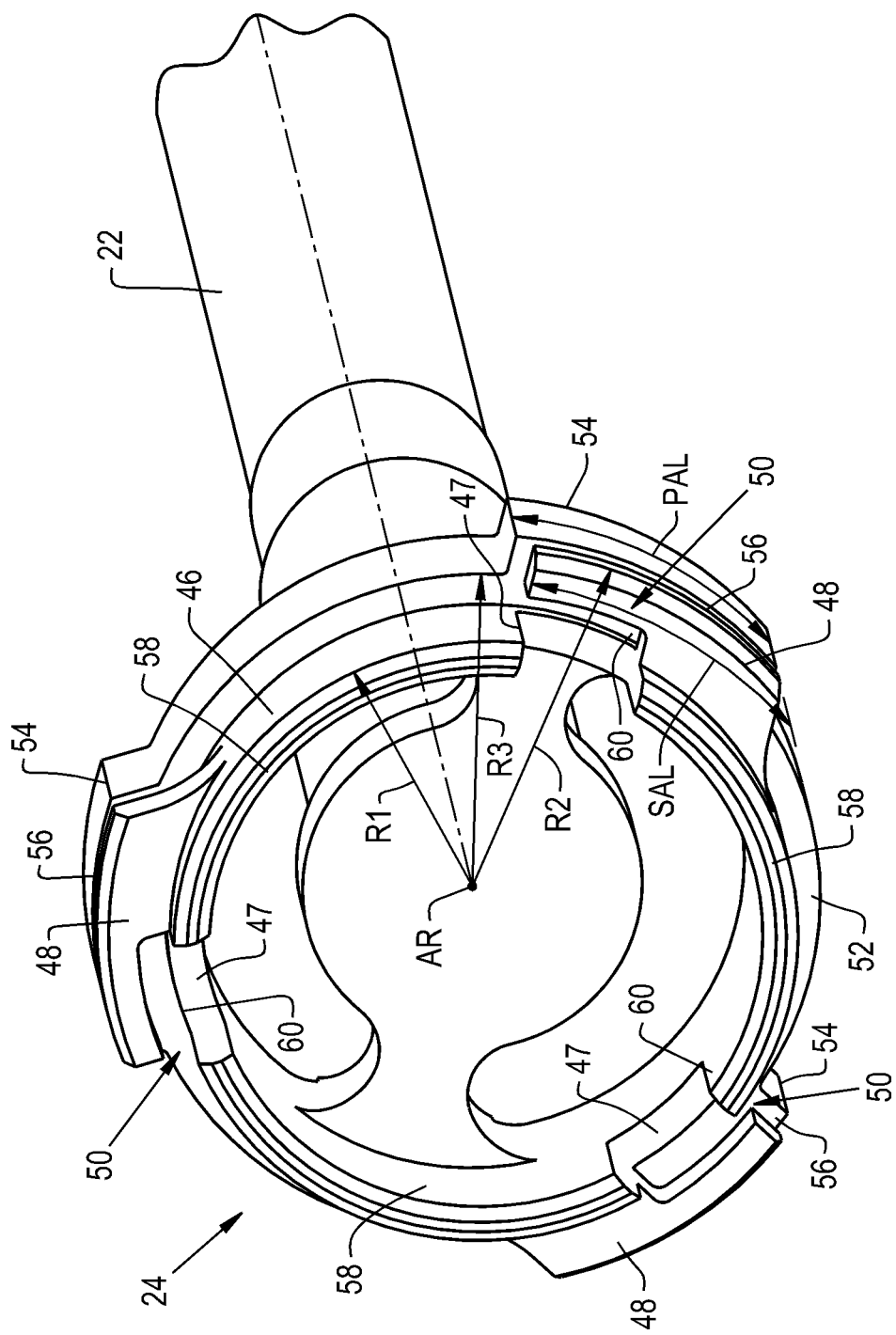
FIG. 3 is a perspective view of a drive shaft and reamer connector of the reamer driver shown in FIGS. 1-2.
Figure 4:
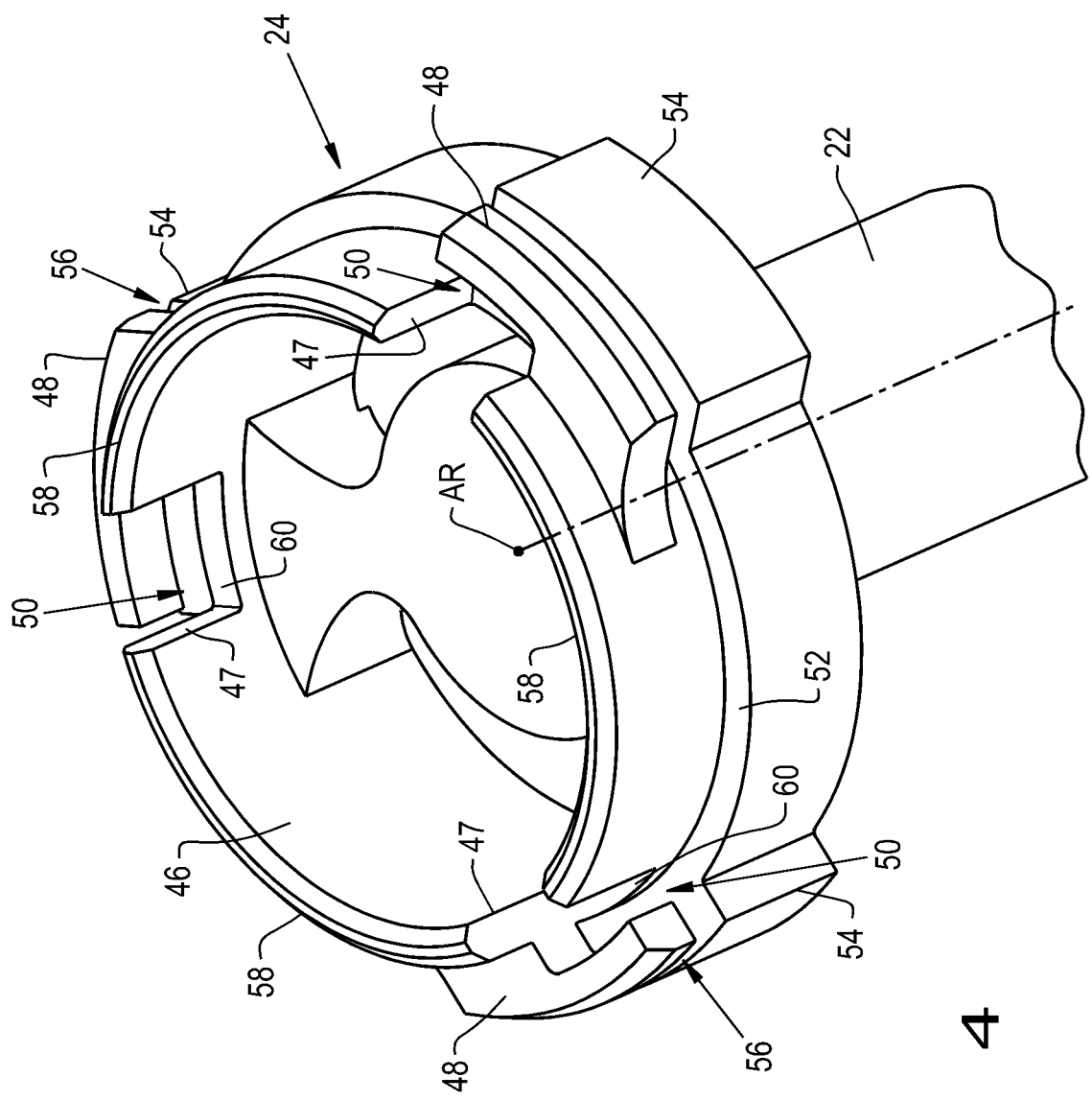
FIG. 4 is another perspective view of the drive shaft and reamer connector shown in FIGS. 1-3.

Referring now to FIGS. 3-4, an exemplary embodiment of the reamer connector 24 and drive shaft 22 formed in accordance with the present invention are shown in more detail. As can be seen, the reamer connector 24 includes one or more first annular portions 46, shown as one first annular portion 46 with a plurality of cutouts 47 formed therein, about the axis of rotation AR defined by the drive shaft 22 and one or more second annular portions 48, shown as three second annular portions 48, about the axis of rotation AR and radially spaced apart from the first annular portion 46 to define one or more holding recesses 50 therebetween, with three such holding recesses 50 being shown. It should be appreciated that while one first annular portion 46 is shown, more than one first annular portion 46 can be included in the reamer connector 22, if desired. The first annular portion 46 can define a first radius R1 relative to the axis of rotation AR and the second annular portions 48 can each define a second radius R2 relative to the axis of rotation AR which is greater than the first radius R1 of the first annular portion 46. Optionally, the reamer connector 24 can also include a rim 52 defined circumferentially about the axis of rotation AR and defining a third radius R3 which is greater than the first radius R1 of the first annular portions 46 and less than the second radius R2 of the second annular portions 48. As used herein, each "radius" R1, R2, R3 of the first annular portion 46, second annular portions 48, and rim 52, respectively, is considered to be the maximum radius relative to the axis of rotation AR defined by the drive shaft 22. The rim 52 can have one or more projections 54 radially extending from the rim 52, with the projection(s) 54 having a projection radius similar or equal to the second radius R2 of the second annular portions 48, as shown. A projection 54 can be formed adjacent to each second annular portion 48 to define a supporting recess 56 therebetween. Similarly, each projection 54 can have a projection arc length PAL which is similar or equal to a second annular arc length SAL of a corresponding second annular portion 48, as shown.

As best shown in FIG. 4, the first annular portion 46 can define three distinguishable upstanding segments 58 between the cutouts 47 formed in the first annular portion 46. Each of the second annular portions 48 can be connected to or integrally formed with one of the upstanding segments 58, if desired. The upstanding segments 58 can be connected to one another by lower segments 60 of the first annular portion 46, which can define the holding recesses 50 with the second annular portions 48. It should be appreciated that the first annular portion 46 may alternatively be a solid ring about the axis of rotation AR with no cutouts formed therein.

Figure 5:
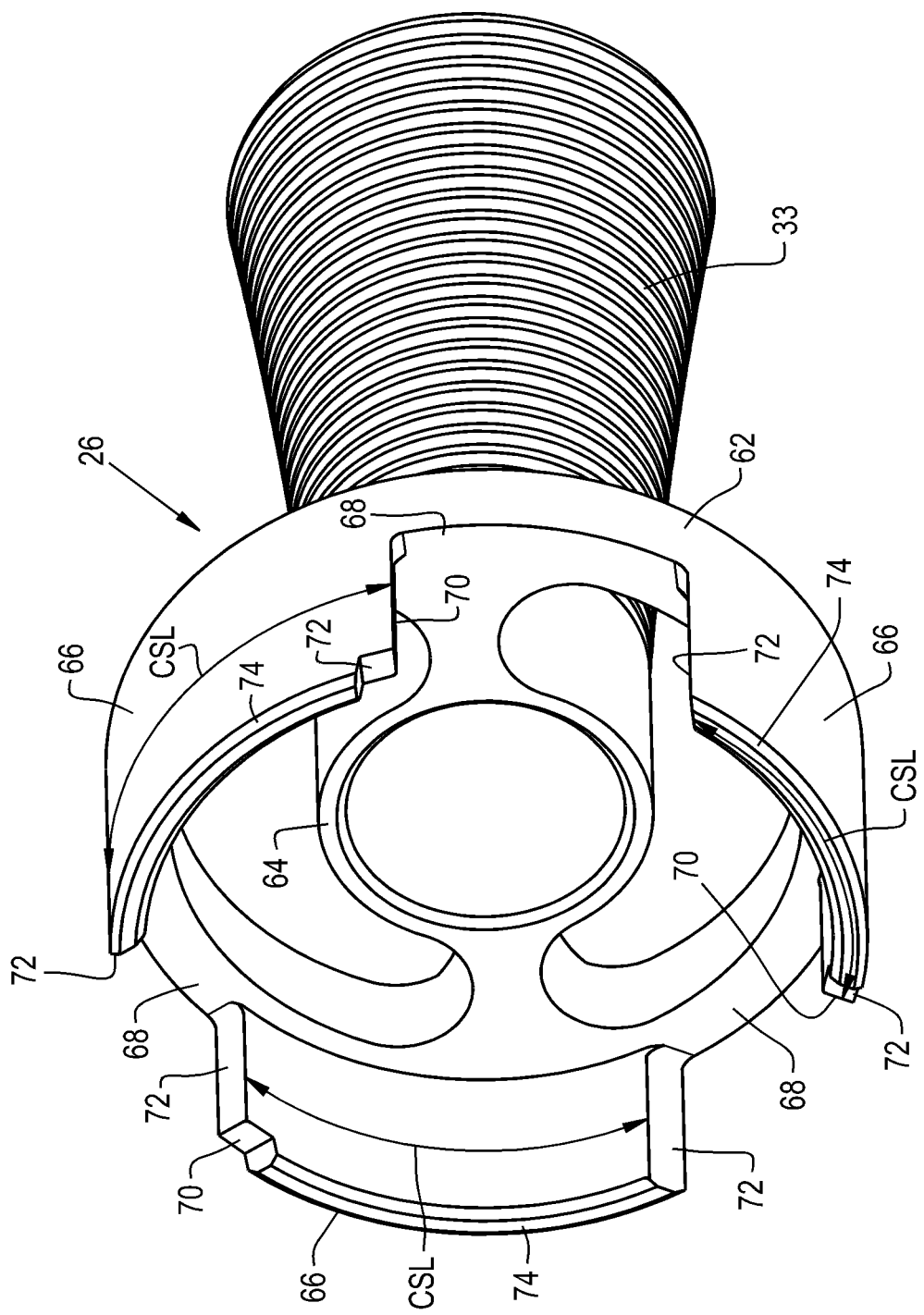
FIG. 5 is a perspective view of a collar of the reamer driver shown in FIGS. 1-2.
Figure 6:
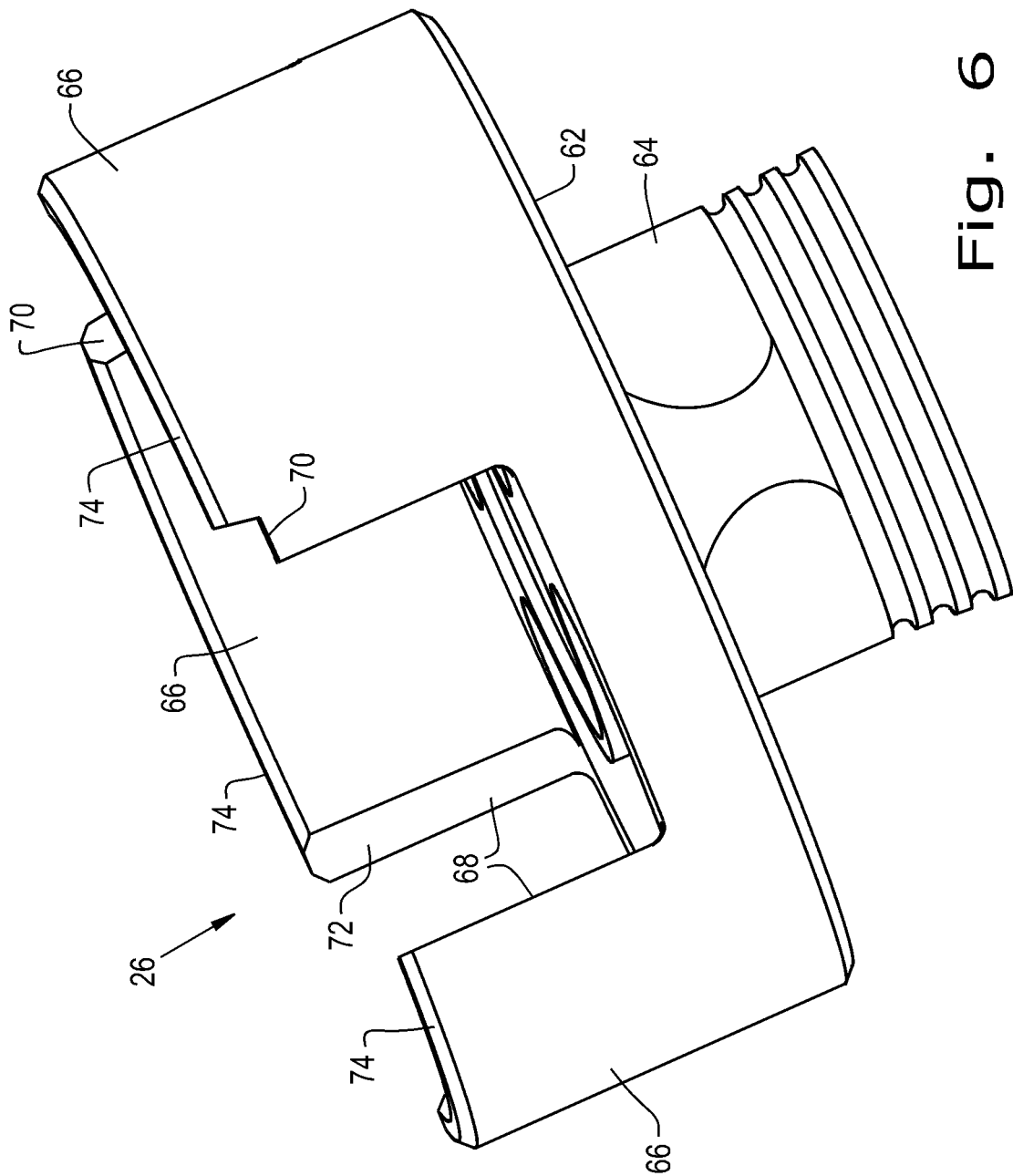
FIG. 6 is another perspective view of the collar shown in FIGS. 1-2 and 5.

Referring now to FIGS. 5-6, an exemplary embodiment of the collar 26 formed according to the present invention is shown in more detail. As can be seen, the collar 26 can include a base ring 62 connected to a cylindrical tube 64 by, for example, being integrally formed with the cylindrical tube 64. The previously described spring 32 can be connected to the cylindrical tube 64, the significance of which will be further described herein. One or more collar segments 66, shown as three collar segments, can extend from the base ring 62 and be distinct from one another by three collar cutouts 68 formed therebetween. The collar cutouts 68 can each be sized and shaped to accept one of the projections 54 of the reamer connector 24 when the collar 26 and reamer connector 24 are rotatably locked together, as will be described further herein. The collar segments 66 may each define an equal collar segment arc length CSL, if desired. Further, each collar segment 66 may have a notch 70 formed in one or both circumferential edges 72 of the collar segment 66; in the shown collar 26, each collar segment 66 only has a notch 70 formed in one of the circumferential edges 72 adjacent a top surface 74 of each collar segment 66.

Figure 7:
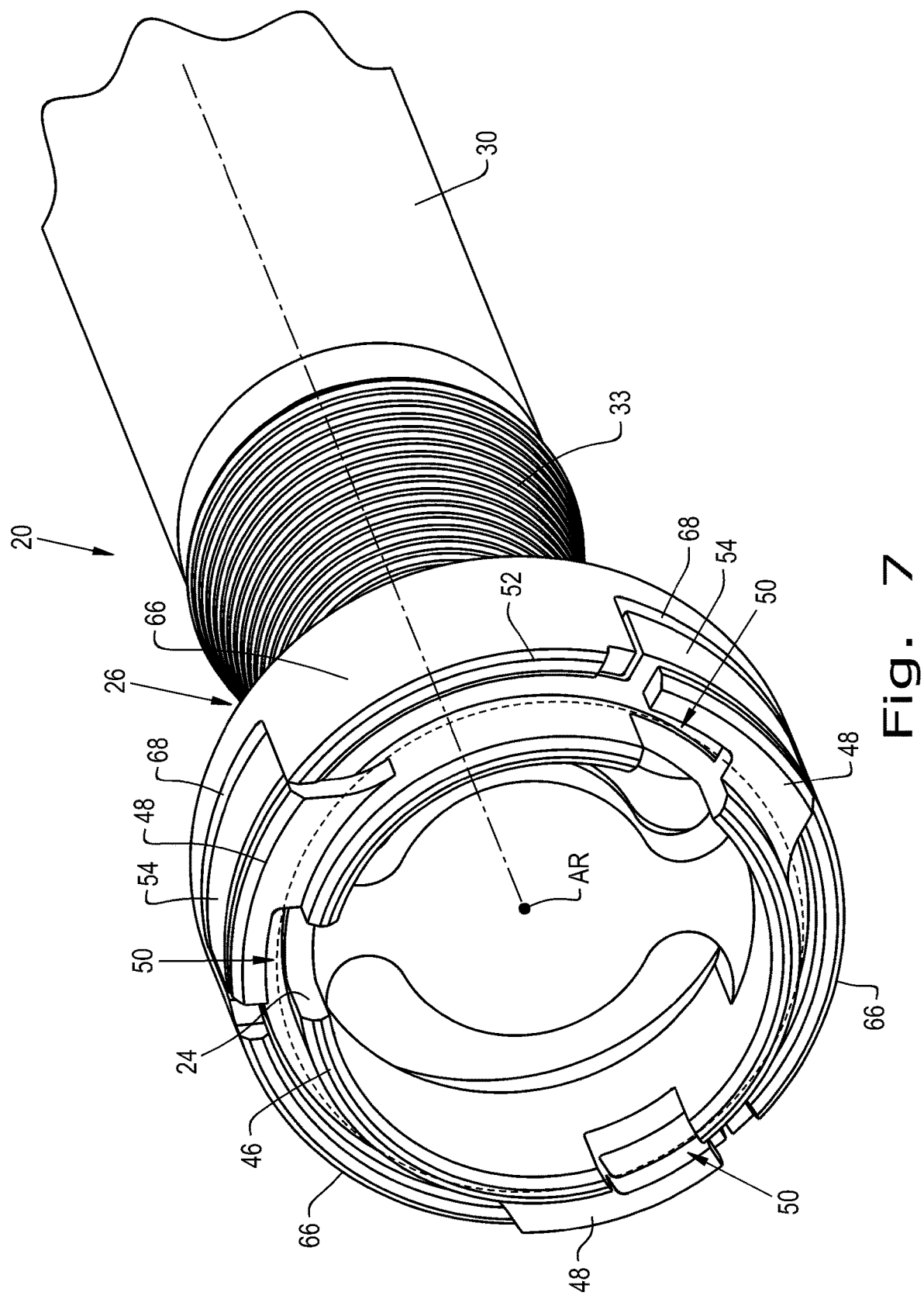
FIG. 7 is a perspective view of the collar shown in FIGS. 1-2 and 5 rotatably locked with the reamer connector shown in FIGS. 1-4.

Referring now to FIG. 7, the assembled reamer driver 20 is shown with the collar 26 in a first position where the collar 26 is unaligned with one or more of the holding recesses 50 circumferentially about the axis of rotation AR defined by the drive shaft 22. As used herein, the collar 26 is "unaligned" with the holding recesses 50 circumferentially about the axis of rotation AR in the sense that no portion of the collar 26, such as the collar segments 66, lies on an imaginary circumference, illustrated in dashed lines, drawn about the axis of rotation AR and extending through one or more of the holding recesses 50, the significance of which will be described further herein. Having the collar 26 unaligned with the holding recesses 50 circumferentially about the axis of rotation AR allows an object held in the holding recess(es) 50 to be rotatable about the axis of rotation AR out of the holding recess(es) 50 without interference from the collar 26.

As shown in FIG. 7, the collar cutouts 68 formed between the collar segments 66 can capture the projections 54 extending from the rim 52 of the reamer connector 24 when the collar 26 is in the first position to rotatably lock the collar 26 to the reamer connector 24. In other words, the projections 54 can fit within the collar cutouts 68 when the collar 26 is in the first position. As the reamer connector 24 is connected to the drive shaft 22 defining the axis of rotation AR, which can connect to a rotary driver, rotatably locking the collar 26 to the reamer connector 24 can also allow the collar 26 to be rotatably driven by the rotary driver during rotation of the drive shaft 22 about the axis of rotation AR. Alternatively, the projections 54 extending from the rim 52 of the reamer connector 24 can be completely located outside the collar cutouts 68 when the collar 26 is in the first position so the collar 26 and reamer connector 24 are not rotatably locked to one another.

Figure 8:
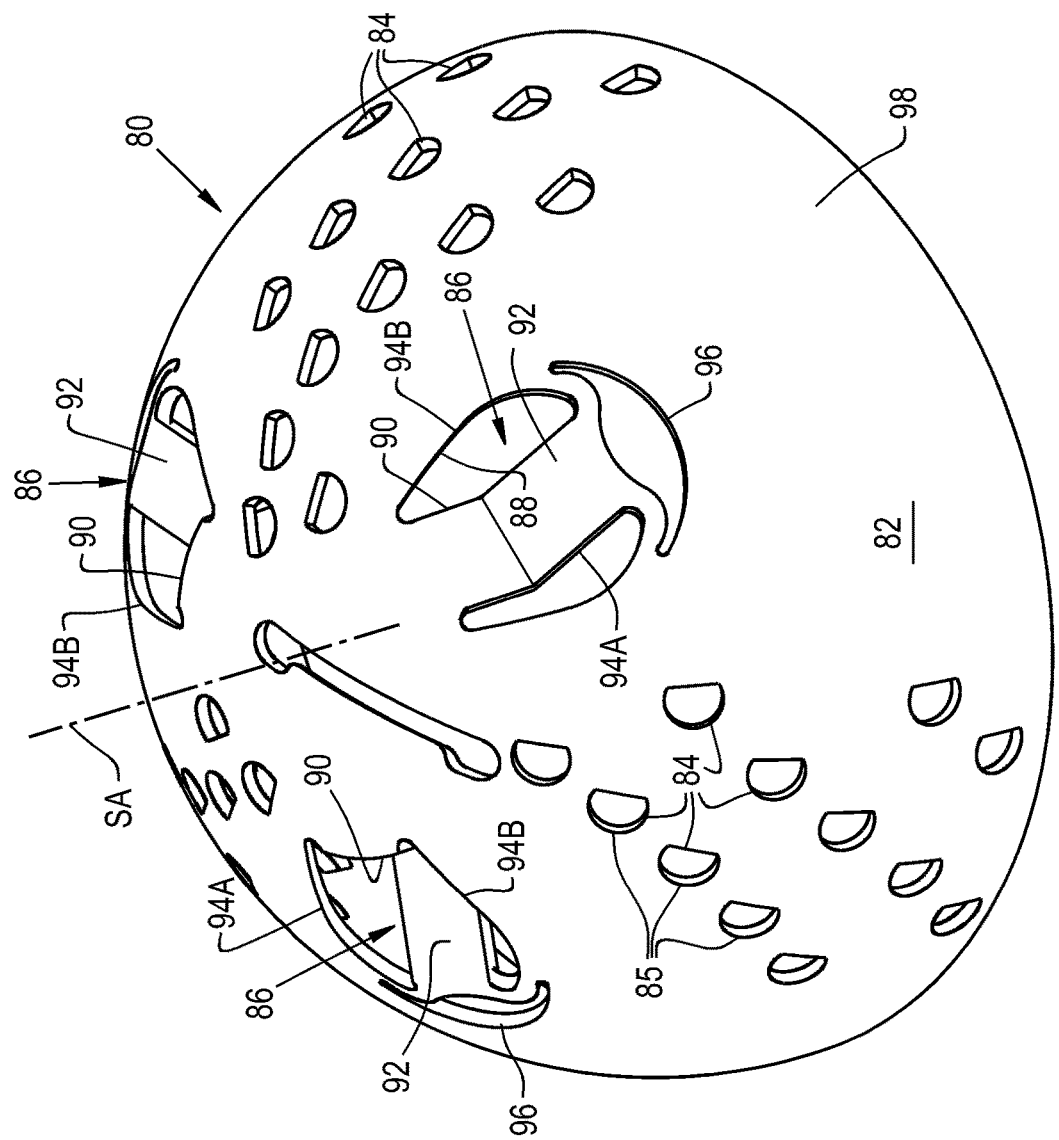
FIG. 8 is a perspective view of an exemplary embodiment of an orthopaedic shell formed in accordance with the present invention.
Figure 9:
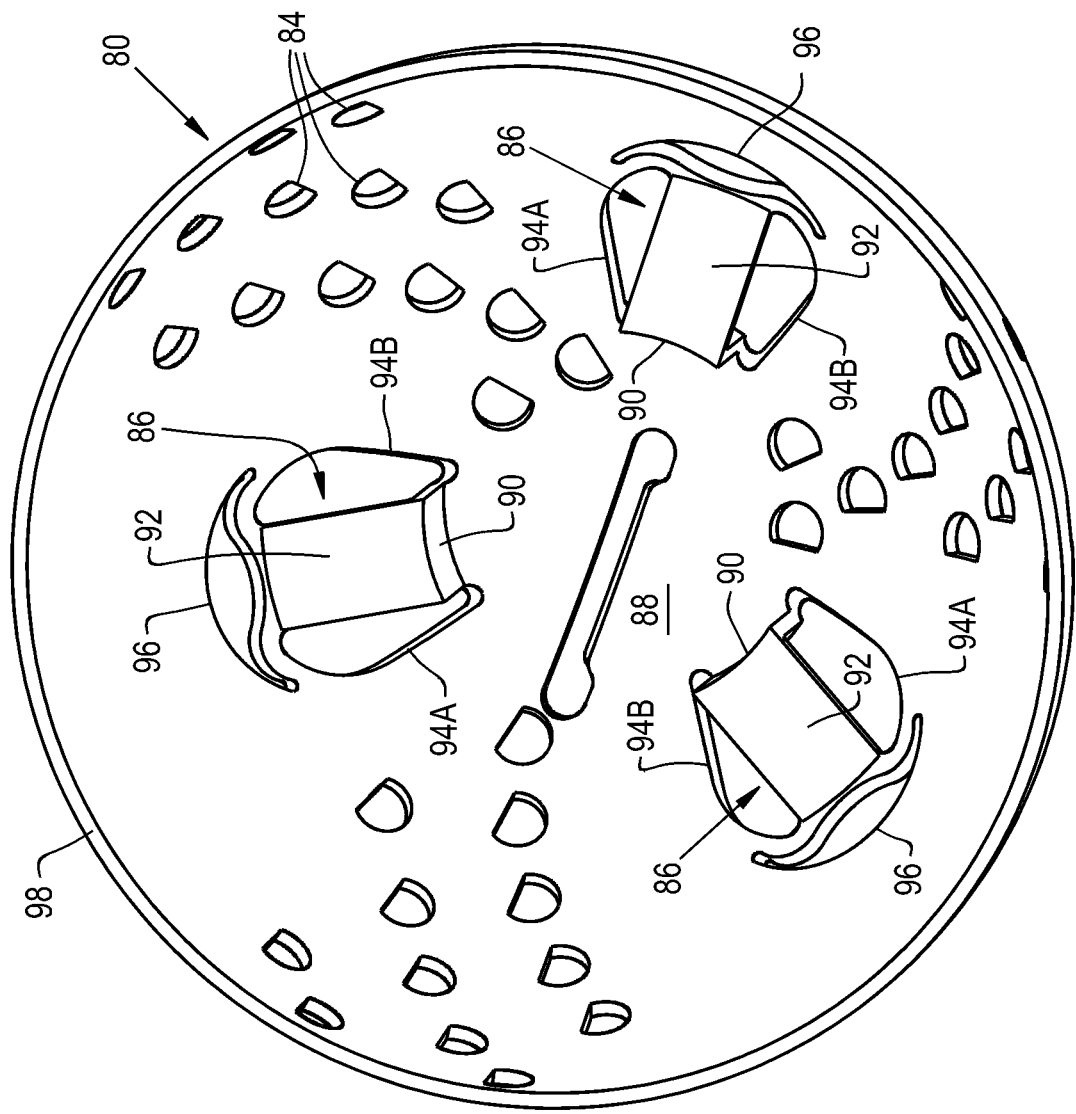
FIG. 9 is another perspective view of the orthopaedic shell shown in FIG. 8.

Referring now to FIGS. 8-9, an exemplary embodiment of an exemplary embodiment of an orthopaedic shell 80, which may also be referred to as "an orthopaedic reamer," formed according to the present invention is shown. The orthopaedic shell 80 can be defined about a shell axis SA and has an outer surface 82 with a plurality of openings 84 formed therein which can be shaped with sharpened edges 85 to cut through bone and other body tissues as the orthopaedic shell 80 rotates within a joint during a surgical procedure. Many different arrangements and shapes of openings 84 formed in the outer surface 82 are known; since the arrangement and shape of the openings 84 on the outer surface 82 can be varied as desired according to the present invention, further description of the exact arrangement and shapes of the openings 84 formed in the outer surface 82 is omitted. The orthopaedic shell 80 has one or more holding tabs 86 which can be formed into an interior 88 of the orthopaedic shell 80 and include a first tab portion 90 extending parallel to the shell axis SA which is connected to a second tab portion 92 extending radially relative to the shell axis SA. While the first tab portion 90 is shown extending parallel to the shell axis SA and the second tab portion 92 is shown extending radially relative to the shell axis SA, i.e., orthogonal to the shell axis SA, other orientations of the tab portions 90, 92 relative to the shell axis SA can be utilized according to the present invention. In some exemplary embodiments, the first tab portion 90 and the second tab portion 92 extend generally perpendicular to one another, but it should be appreciated that the first tab portions 90 and second tab portions 92 can extend to form other angles. The orthopaedic shell 80 can also have a pair of mirrored slots 94A, 94B formed on opposite sides of the holding tabs 86, as well as an additional slot 96 formed between the holding tabs 86 and a rim 98 of the orthopaedic shell 80.

Figure 10:
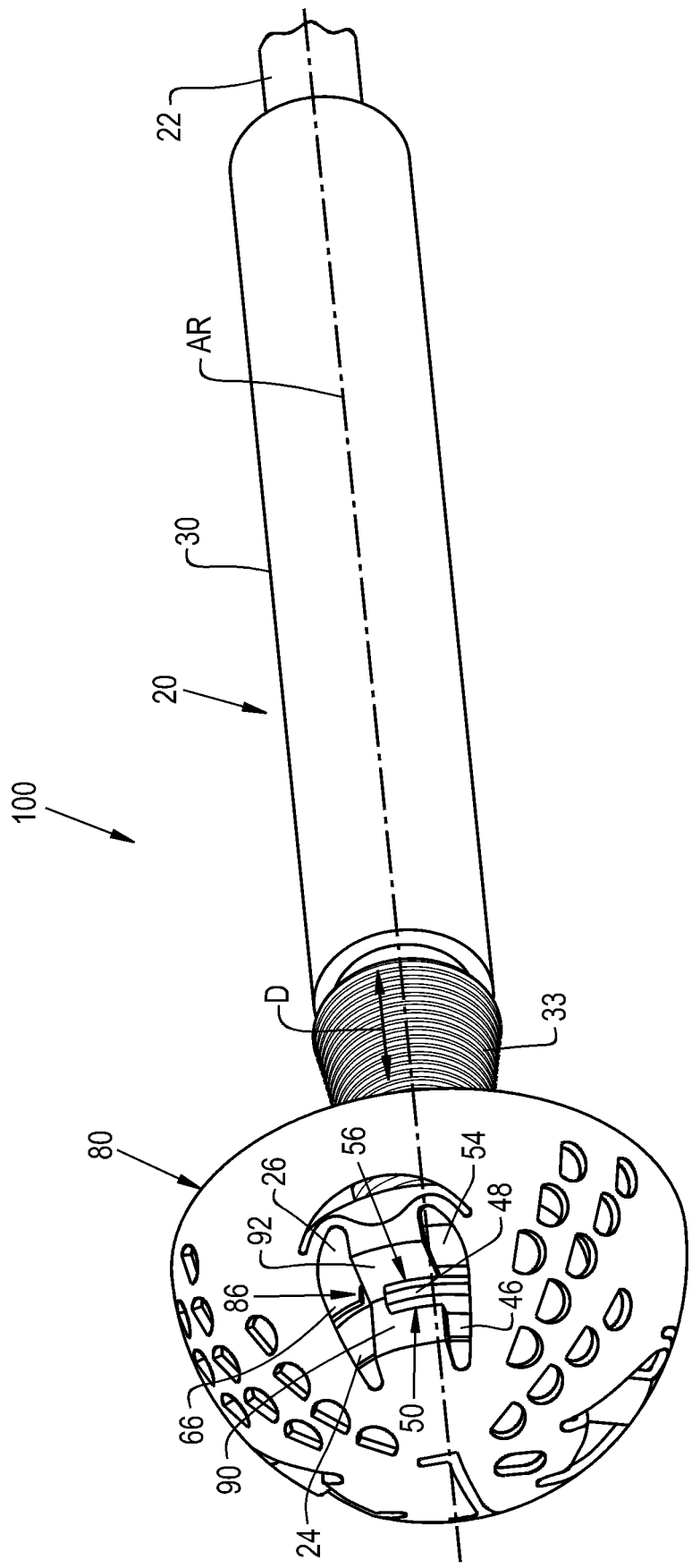
FIG. 10 is a perspective view of an exemplary embodiment of an orthopaedic reamer system formed in accordance with the present invention which includes the orthopaedic shell shown in FIGS. 8-9 rotatably locked to the reamer driver shown in FIGS. 1-2 and 7.
Figure 11:
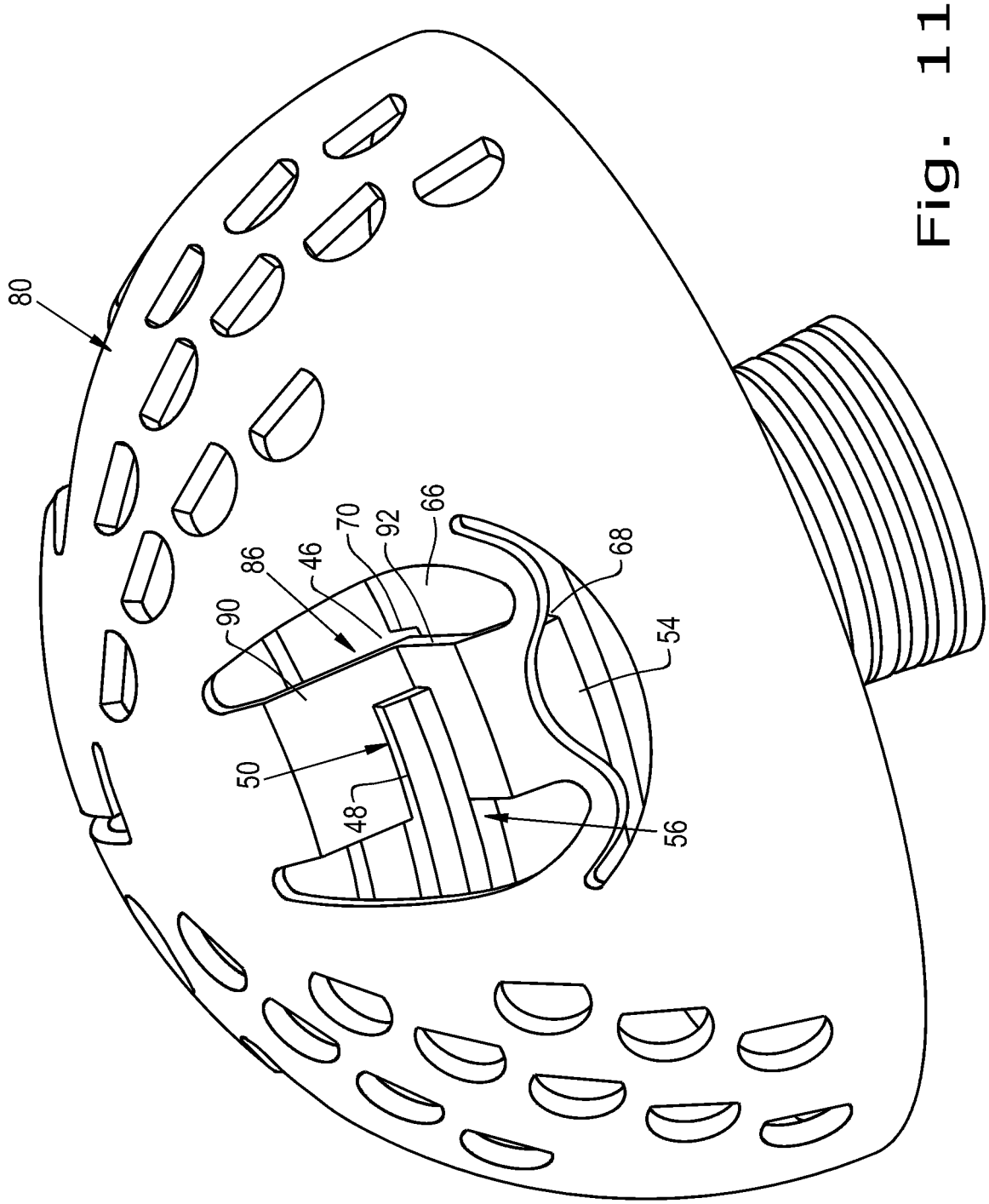
FIG. 11 is another perspective view of the orthopaedic reamer system shown in FIG. 10.

Referring now to FIGS. 10-11, an exemplary embodiment of an orthopaedic reamer system 100 formed according to the present invention is shown which includes the orthopaedic shell 80 rotatably locked to the reamer driver 20. As can be seen, the holding tabs 86 formed in the orthopaedic shell 80 are placed within the holding recesses 50 of the reamer connector 24 and the collar 26 is placed in the second position such that the collar segments 66 rotatably lock the holding tabs 86 within the holding recesses 50, i.e., the holding tabs 86 cannot freely rotate out of the holding recesses 50 when the collar 26 is in the second position. More specifically, the first tab portions 90 of the holding tabs 86 can be placed within the holding recesses 50 while the second tab portions 92 of the holding tabs 86 can be placed within the supporting recesses 56 so the holding tabs 86 are stably held between the first annular portion 46 and the second annular portions 48 as well as between the second annular portions 48 and the rim 52 of the reamer connector 24, with the collar 26 in the second position obstructing rotation of the holding tabs 86 out of the holding recesses 50 and, therefore, rotatably locking the orthopaedic shell 80 to the reamer connector 24. To remove the orthopaedic shell 80 from the reamer connector 24, a user can pull the collar 26 in the direction D against the biasing force provided by the spring 32 so the collar 26 axially slides along the drive shaft 22 toward the sleeve 30 bearing against the spring 32 and becomes unaligned with the holding recesses 50 circumferentially about the axis of rotation AR, allowing the orthopaedic shell 80 to be rotatable out of the holding recesses 50 and removable from the reamer connector 24. It should therefore be appreciated from the foregoing description that exemplary embodiments of the orthopaedic reamer system 100 formed in accordance with the present invention provide for quick disconnection of the orthopaedic shell 80 from the reamer connector 24 by sliding the collar 26 in a direction D along the axis of rotation AR to different positions.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A driver for an orthopaedic reamer, comprising:
   a drive shaft defining an axis of rotation;
   a reamer connector connected to said drive shaft and having at least one first annular portion about said axis of rotation and at least one second annular portion about said axis of rotation radially spaced from said at least first annular portion to define at least one holding recess therebetween, said reamer connector including a rim defined circumferentially about said axis of rotation and at least one protrusion projecting radially from said rim, said at least one protrusion and said at least one second annular portion defining a supporting recess therebetween; and
   a collar associated with said reamer connector and slideable in a direction along said axis of rotation between a first position and a second position, said collar being unaligned with said at least one holding recess circumferentially about said axis of rotation in said first position and, in said second position, being rotatably locked to said reamer connector and having a portion aligned with said at least one holding recess circumferentially about said axis of rotation.

2. The driver according to claim 1, wherein said at least one first annular portion defines a first radius relative to said axis of rotation, said at least one second annular portion defines a second radius relative to said axis of rotation, and said rim defines a third radius relative to said axis of rotation, said third radius being less than said second radius and greater than said first radius.

3. The driver according to claim 1, wherein said collar includes at least one cutout formed therein, said at least one protrusion fitting within said at least one cutout when said collar is in said second position.

4. The driver according to claim 3, further comprising a biasing element configured to bias said collar toward said second position.

5. The driver according to claim 4, further comprising a sleeve placed over said drive shaft and bearing against said biasing element.

6. The driver according to claim 1, wherein said collar is axially slideable along said drive shaft in said direction along said axis of rotation between said first position and said second position.

7. An orthopaedic reamer system, comprising:
a drive shaft defining an axis of rotation;
a reamer connector connected to said drive shaft and having at least one first annular portion about said axis of rotation and at least one second annular portion about said axis of rotation radially spaced from said at least first annular portion to define at least one holding recess therebetween;
an orthopaedic shell having an outer surface with a plurality of openings formed therein and at least one holding tab placed within said at least one holding recess; and
a collar associated with said reamer connector and slideable in a direction along said axis of rotation between a first position and a second position, said at least one holding tab being rotatable out of said at least one holding recess when said collar is in said first position, said collar being rotatably locked to said reamer connector and rotatably locking said at least one holding tab within said at least one holding recess in said second position, the at least one holding tab being placed within the at least one holding recess such that rotation of the reamer connector and the collar about the axis of rotation causes abutment of the at least one holding tab against at least one of an end of the at least one holding recess or the collar to rotate the orthopaedic shell.

8. The orthopaedic reamer system according to claim 7, wherein said reamer connector includes a rim defined circumferentially about said axis of rotation.

9. The orthopaedic reamer system according to claim 8, wherein said at least one first annular portion defines a first radius relative to said axis of rotation, said at least one second annular portion defines a second radius relative to said axis of rotation, and said rim defines a third radius relative to said axis of rotation, said third radius being less than said second radius and greater than said first radius.

10. The orthopaedic reamer system according to claim 8, wherein said reamer connector includes at least one protrusion projecting radially from said rim and said collar includes at least one cutout formed therein, said at least one protrusion fitting within said at least one cutout when said collar is in said second position.

11. The orthopaedic reamer system according to claim 10, further comprising a biasing element configured to bias said collar toward said second position.

12. The orthopaedic reamer system according to claim 11, further comprising a sleeve placed over said drive shaft and bearing against said biasing element.

13. The orthopaedic reamer system according to claim 10, wherein said at least one protrusion and said at least one second annular portion define a supporting recess therebetween.

14. The orthopaedic reamer system according to claim 13, wherein said orthopaedic shell defines a shell axis and said at least one holding tab defines a first tab portion extending parallel to said shell axis and a second tab portion extending radially relative to said shell axis, said first tab portion being held within said at least one holding recess and said second tab portion being held within said supporting recess.

15. The orthopaedic reamer system according to claim 7, wherein said collar is axially slideable along said drive shaft in said direction along said axis of rotation between said first position and said second position.

16. The orthopaedic reamer system according to claim 7, wherein the at least one holding tab is placed within the at least one holding recess such that rotation of the reamer connector and the collar about the axis of rotation causes abutment of the at least one holding tab against the end of the at least one holding recess to rotate the orthopaedic shell.

* * * * *